United States Patent
Band et al.

(10) Patent No.: US 11,351,031 B2
(45) Date of Patent: Jun. 7, 2022

(54) APPLICATIONS OF DIFFUSION HARDENING TECHNIQUES

(71) Applicant: Smith & Nephew, Inc., Memphis, TN (US)

(72) Inventors: Timothy John Band, Matlock Bath (GB); Hamish Forster, Memphis, TN (US); Gordon Bruce Hunter, Germantown, TN (US); Shilesh C. Jani, Memphis, TN (US); Mark Lee Morrison, Memphis, TN (US); Vivek Devidas Pawar, Germantown, TN (US); Abraham Biglari Salehi, Bartlett, TN (US); Jeffrey Joel Shea, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 335 days.

(21) Appl. No.: 16/688,207

(22) Filed: Nov. 19, 2019

(65) Prior Publication Data
US 2020/0078179 A1 Mar. 12, 2020

Related U.S. Application Data

(60) Continuation of application No. 15/723,735, filed on Oct. 3, 2017, now Pat. No. 10,512,544, which is a
(Continued)

(51) Int. Cl.
*A61F 2/30* (2006.01)
*A61L 27/04* (2006.01)
(Continued)

(52) U.S. Cl.
CPC ........ *A61F 2/30767* (2013.01); *A61L 27/045* (2013.01); *A61L 27/306* (2013.01);
(Continued)

(58) Field of Classification Search
CPC .......... A61F 2/30767; A61F 2/32; A61F 2/34; A61F 2/36; A61F 2/3662; A61F 2/3859;
(Continued)

(56) References Cited

U.S. PATENT DOCUMENTS 4,743,262 A 5/1988 Tronzo
4,790,888 A * 12/1988 Bessey ............... C21D 1/72
148/23

(Continued)

FOREIGN PATENT DOCUMENTS

CA 2597266 A1 8/2006
EP 1582756 A2 10/2005
(Continued)

OTHER PUBLICATIONS

ASM International, Materials Park, Ohio, Heat Treating, "Plasma (Ion) Nitriding", Aug. 1991, vol. 4, pp. 420-424.
(Continued)

*Primary Examiner* — Yashita Sharma
*Assistant Examiner* — Jared Klar Rovira
(74) *Attorney, Agent, or Firm* — KDB

(57) ABSTRACT

A device, for example a medical implant, and a method of making the same, the device having a metal or metal alloy substrate, for example cobalt chrome, and a diffusion hardened metallic surface, for example a plasma carburized surface, contacting a non-diffusion hardened surface or a diffusion hardened surface having a diffusion hardening species different from that of the opposing surface.

21 Claims, 6 Drawing Sheets

Related U.S. Application Data division of application No. 12/161,529, filed as application No. PCT/US2007/060719 on Jan. 18, 2007, now Pat. No. 9,775,713.

(60) Provisional application No. 60/759,843, filed on Jan. 18, 2006.

(51) Int. Cl.

| | |
|---|---|
| *A61L 27/30* | (2006.01) |
| *A61L 27/50* | (2006.01) |
| *C23C 8/00* | (2006.01) |
| *C23C 8/36* | (2006.01) |
| *A61F 2/32* | (2006.01) |
| *A61F 2/34* | (2006.01) |
| *A61F 2/36* | (2006.01) |
| *A61F 2/38* | (2006.01) |
| *A61F 2/40* | (2006.01) |
| *A61F 2/42* | (2006.01) |
| *A61F 2/44* | (2006.01) |

(52) U.S. Cl.
CPC ............... *A61L 27/50* (2013.01); *C23C 8/00* (2013.01); *C23C 8/36* (2013.01); *A61F 2/3094* (2013.01); *A61F 2/3099* (2013.01); *A61F 2/32* (2013.01); *A61F 2/34* (2013.01); *A61F 2/36* (2013.01); *A61F 2/367* (2013.01); *A61F 2/3662* (2013.01); *A61F 2/38* (2013.01); *A61F 2/3804* (2013.01); *A61F 2/389* (2013.01); *A61F 2/3859* (2013.01); *A61F 2/40* (2013.01); *A61F 2/4241* (2013.01); *A61F 2/44* (2013.01); *A61F 2002/30878* (2013.01); *A61F 2002/30892* (2013.01); *A61F 2002/30922* (2013.01); *A61F 2002/30934* (2013.01); *A61F 2002/365* (2013.01); *A61F 2002/3611* (2013.01); *A61F 2002/3625* (2013.01); *A61F 2310/00029* (2013.01); *A61F 2310/0058* (2013.01); *A61F 2310/0067* (2013.01); *A61F 2310/0073* (2013.01); *A61F 2310/0088* (2013.01); *A61F 2310/00598* (2013.01); *A61F 2310/00604* (2013.01); *A61F 2310/00748* (2013.01); *A61F 2310/00754* (2013.01); *A61F 2310/00856* (2013.01); *A61F 2310/00868* (2013.01); *A61F 2310/00886* (2013.01); *Y02T 50/60* (2013.01)

(58) Field of Classification Search
CPC .. A61F 2002/30922; A61F 2002/30934; A61F 2002/3611; A61F 2002/365; A61F 2310/00029; A61F 2310/00598; A61F 2310/00604; A61F 2310/0067; A61F 2310/0073; A61F 2310/00748; A61F 2310/00754; A61L 27/045; A61L 27/50; C23C 8/00
See application file for complete search history.

(56) References Cited

U.S. PATENT DOCUMENTS

| | | |
|---|---|---|
| 5,152,794 A | 10/1992 | Davidson |
| 5,180,394 A | 1/1993 | Davidson |
| 5,308,412 A | 5/1994 | Shetty et al. |
| 5,415,704 A | 5/1995 | Davidson |
| 6,641,893 B1 | 11/2003 | Suresh et al. |
| 7,060,102 B2 | 6/2006 | Thompson et al. |
| 2003/0125808 A1 | 7/2003 | Hunter et al. |
| 2005/0228390 A1 | 10/2005 | Cutshall et al. |
| 2005/0241736 A1 | 11/2005 | Beil et al. |
| 2006/0048856 A1 | 3/2006 | Li et al. |

FOREIGN PATENT DOCUMENTS

| | | |
|---|---|---|
| JP | 05240253 A | 9/1993 |
| JP | 05291495 A | 11/1993 |
| WO | 1997016138 A1 | 5/1997 |
| WO | 2001054561 A2 | 8/2001 |
| WO | 2006044576 A1 | 4/2006 |

OTHER PUBLICATIONS

Australian Office Action; Application No. 2007205890; dated Oct. 20, 2010.
Australian Patent Office; Patent Examination Report No. 1; dated May 17, 2013; 3 pages.
Australian Examination Report; Australian Patent Office; Australian Application No. 2015203048; dated Jan. 7, 2016; 3 pages.
Office Action in Chinese Patent Appiication No. 200780009305.7, dated Nov. 24, 2011, 19 pages.
Office Action; State Intellectual Property Office of the People's Republic of China; Chinese Patent Application No. 200780009305.7; Apr. 4, 2014; 7 pages.
European Examination Report; European Patent Office; European Application No. 07717307.8; dated Nov. 14, 2016; 4 pages.
Japanese Office Action, Application No. 2008-551534, dated Nov. 1, 2011, 4 pages.
International Search Report and Written Opinion issued for PCT/US2007i060719, dated Nov. 27, 2007, 7 pages.

* cited by examiner

APPLICATIONS OF DIFFUSION HARDENING TECHNIQUES

CROSS-REFERENCE TO RELATED APPLICATIONS

This application is a continuation of U.S. patent application Ser. No. 15/723,735 filed on Oct. 3, 2017, which is a divisional of U.S. patent application Ser. No. 12/161,529 filed on Jul. 18, 2008 and now issued as U.S. Pat. No. 9,775,713, which is a U.S. National Phase of International PCT Application No. PCT/US2007/060719 filed Jan. 18, 2007, which claims the benefit of U.S. Provisional Patent Application Ser. No. 60/759,843 filed on Jan. 18, 2006, the contents of each application hereby incorporated by reference in their entirety.

TECHNICAL FIELD

This invention pertains to devices having metallic surfaces which contact other metallic surfaces. In preferred embodiments, the invention pertains to a hard-on-hard medical implant. Preferably, the invention pertains to a medical implant having a metal or metal alloy substrate and a carburized surface articulating against a non-carburized surface.

BACKGROUND OF THE INVENTION

Medical implant materials, in particular orthopedic implant materials, must combine high strength, corrosion resistance and tissue compatibility. The longevity of the implant is of prime importance especially if the recipient of the implant is relatively young because it is desirable that the implant function for the entire lifetime of a patient. Because certain metal alloys have the required mechanical strength and biocompatibility, they are ideal candidates for the fabrication of prostheses. These alloys include 316L stainless steel, chrome-cobalt-molybdenum alloys (CoCr), titanium alloys and more recently zirconium alloys which have proven to be the most suitable materials for the fabrication of load-bearing and non-load bearing prostheses.

In a traditional hip implant, CoCr alloy femoral head articulates against polyethylene. Owing to the relative hardness of each of the articulating components, this type of implant is frequently referred to in the art as a hard-on-soft implant; the CoCr alloy being the hard component of the articulating couple, and the polyethylene being the corresponding soft component. During the life of the implant, wear of the polyethylene exceeds that of the hard component. The polyethylene wear debris in turn may lead to osteolysis and loosening of the implant. A considerable amount of effort has been expended in the prior art in an effort to reduce this wear. One of the approaches has been to change the characteristics of polyethylene to improve its wear characteristics, for example by cross-linking. Another approach has been to change the characteristics of the femoral head. One such approach has been taught by Davidson (U.S. Pat. No. 5,037,438). Davidson recommends use of an oxidized zirconium surface to reduce the wear of polyethylene. Even though such approaches have led to significant reduction in wear of polyethylene, there has been a growing demand for much more wear resistant implants. This need comes from young and active patients who want to return to their normal lives after the joint replacement. Another requirement of these young and active patients is the joint stability. Typically, a larger-anatomical joint is more stable than a smaller joint. Polyethylene due to its lower strength can not be made beyond certain sizes and thus limits its use for young and active patients. This has led to emergence of hard-on-hard metal implants.

Currently, there are two primary types of hard-on-hard hip implants that are available commercially. These are metal-on-metal (including metal alloy-on-metal alloy) and ceramic-on-ceramic. The current standard material of metal-on-metal implants is high carbon CoCr alloy. The major concern with the metal-on-metal implant is the metal ion release from the joint and its unknown effects on the physiology of the human body. The advantage of metal-on-metal implants is that they can be used in larger sizes. The larger size of the implant allows greater range of motion and can provide more joint stability. The metal-on-metal implants have also been shown to be useful for resurfacing type of application where conservation of bone is desired. In such larger joints, the conventional or cross-linked polyethylene is not preferred and metal-on-metal may be the only choice available. The larger size requires polyethylene liner to be thinner. A thinner liner may not be mechanically strong, may creep more or may lead to increased wear and osteolysis and eventually failure of the implant. In general, the class of hard-on-hard implants can be significantly broadened. It can include components articulating against each other that are made from metals or ceramics or any combinations thereof. In this disclosure, the term hard refers to metals and or ceramics. Thus "hard-on-hard" can be metal-on-metal, metal-on-ceramic, and ceramic-on-ceramic. In the foregoing context, "metal" includes both pure metals and metal alloys.

The other commonly used hard-on-hard joint is ceramic-on-ceramic. The current standard material of ceramic-on-ceramic implants is alumina. Metal ion release is typically not a concern for these implants. But due to limited toughness and brittle nature of ceramics, it is difficult to make these implants in larger sizes. The ceramic components have finite probability of fracture thus leading to a potential joint failure and complications associated with the fracture of a joint.

It has been an object of much of the prior art to reduce the metal ion release and minimize the fracture risk by combining metal and ceramic components. Fisher at al. (U.S. Patent Application 2005/0033442) and Khandkar et al. (U.S. Pat. No. 6,881,229) teach the use of an implant having a metal-on-ceramic articulation. Fisher et al teach that the difference in hardness between the metallic component and the ceramic component to be at least 4000 MPa. Khandkar et. al. specifically teach use of silicon nitride ceramic components for articulating against the metallic component. In both instances, the objective is to lower the wear of mating couples. But in both instances, the fracture risk of ceramic is still significant. In both instances, the strength of ceramic component influences how large the joint size can be made. It should be noted that in both instances it is the ceramic surface that is mating with a metallic surface. As discussed in the details below, the object of this invention is to reduce the wear of the mating couples when both component surfaces are metallic in nature. In another approach, Lippincott and Medley (U.S. Pat. No. 6,059,830) teach applying geometrical constraints to the mating hip components. The '830 patent teaches the use of components such that the radius difference of the mating components is less than 50 microns. This small difference in radius will promote thicker fluid film formation and thus reduced wear of mating metallic components. The disadvantage of this method is that a sophisticated manufacturing set-up is required to produce components with such tight tolerances.

The problems relating to a low wear hard-on-hard metallic couple is not unique to the medical implant field, and exists in other fields of art as well, examples of which include automotive and aerospace components. Other bearing applications would also benefit from an improved couple.

The inventors of the present invention have found that such a demanding manufacturing approach is not necessary because significant improvements in wear reduction can be realized through the differential treatment of one surface of two contacting surfaces, and in particular where the contacting surfaces articulate against one another.

BRIEF SUMMARY OF THE INVENTION

The present invention is directed to a medical implant, and a method of making the same, having a metal or metal alloy substrate, for example CoCr, and a diffusion hardened, surface, for example a plasma carburized surface, contacting a non-diffusion hardened surface or a diffusion hardened surface having a diffusion hardening species different from that of the opposing surface.

In one embodiment, there is device comprising: a first portion, said first portion having a first contacting surface; a second portion, said second portion having a second contacting surface; wherein the first portion and the second portion are comprised of metal or metal alloy, and wherein the first and second contacting surfaces contact one another; and, wherein one of conditions (a) and (b) is met: (a) one of said first and second contacting surfaces comprises a diffusion hardened metallic surface which is diffusion hardened with a diffusion hardening species and the other of said first and second contacting surfaces is a metallic surface that is not diffusion hardened; (b) both of said first and second contacting surfaces comprise a diffusion hardened metallic surface wherein said first contacting surface is diffusion hardened with at least a first diffusion hardening species and said second contacting surface is diffusion hardened with at least a second diffusion hardening species and wherein said first diffusion hardening species is different from said second diffusion hardening species; wherein said diffusion hardening species is selected from the group consisting of carbon, nitrogen, oxygen, boron, and any combination thereof. In another embodiment, the device is a medical implant. In some embodiments, the metal or metal alloy comprising said first portion is different from the metal or metal alloy comprising said second portion. In some embodiments of the device, the metal or metal alloy is CoCr. In some embodiments of the device, one or both of said contacting surfaces comprises a plasma hardened surface. In some embodiments of the device, the plasma hardened surface is selected from the group consisting of a plasma carburized surface, a plasma nitrided surface, a plasma oxidized surface, a plasma borided surface and any combination thereof. In some embodiments wherein the device is a medical implant, the medical implant is a hip implant. In some hip implant embodiments, one of said first portion and second portion is a femoral component comprising a femoral head and wherein said femoral head comprises a contacting surface; and wherein the other of said first portion and second portion is an acetabular component, said acetabular component comprising a inner surface wherein said inner surface comprises a contacting surface. In some hip implant embodiments, one or both of said contacting surfaces comprises a plasma hardened surface. In some hip implant embodiments, said plasma hardened surface is selected from the group consisting of a plasma carburized surface, a plasma nitrided surface, a plasma oxidized surface, a plasma borided surface and any combination thereof. In some medical implant embodiments, the medical implant is a knee implant. In some knee implant embodiments, one of said first portion and second portion is a femoral component comprising at least one condyle, said at least one condyle comprising a contacting surface, and wherein the other of said first portion and second portion is a tibial component, said tibial component comprising a contacting surface. In some knee implant embodiments, one or both of said contacting surfaces comprises a plasma hardened surface. In some knee implant embodiments, said plasma hardened surface is selected from the group consisting of a plasma carburized surface, a plasma nitrided surface, a plasma oxidized surface, a plasma borided surface and any combination thereof. In some medical implant embodiments, the medical implant is selected from the group consisting of a shoulder implant, an elbow implant, a finger implant, a vertebral implant, and a tempro-mandibular implant. In some embodiments of the device, said first contacting surface and said second contacting surface articulate against one another. In some embodiments of the device, the device further comprises a deposited ceramic coating on one or both of said first and second contacting surfaces. In some embodiments of the device comprising a deposited ceramic coating, said deposited ceramic coating is selected from the group consisting of ceramic oxides, ceramic nitrides, ceramic carbides, ceramic borides, and any combination thereof. In some embodiments of the device, the device further comprises a diamond or diamond-like carbon coating on one or both of said first and second contacting surfaces. In some embodiments of the device, both of said first and second contacting surfaces comprise a diffusion hardened metallic surface and wherein said first contacting surface is diffusion carburized and diffusion oxidized, and said second contacting surface is diffusion carburized. In some embodiments of the device, condition (b) applies and, said diffusion hardening species for said first contacting surface is selected from the group consisting of carbon, nitrogen, boron, and any combination thereof; and, said diffusion hardening species for said second contacting surface is selected from the group consisting of carbon, nitrogen, oxygen, boron, and any combination thereof, subject to the condition that one of said contacting surfaces is diffusion hardened with a diffusion hardening species that is not present as a diffusion hardening species in the other contacting surface. In some embodiments of the device, said diffusion hardening species is selected from the group consisting of carbon, nitrogen, oxygen, and any combination thereof. In some embodiments of the device, the device is an automotive or aerospace device.

In another embodiment, there is a method of making a device comprising the steps of: forming a device from a metal or metal alloy, said device comprising a first portion, said first portion having a first contacting surface, and a second portion, said second portion having a second contacting surface, wherein said first and second contacting surfaces contact one another; forming a diffusion hardened metallic surface on said device by diffusion hardening, said step of diffusion hardening being performed with a diffusion hardening species selected from the group consisting of carbon, nitrogen, oxygen, boron, and any combination thereof, said step of diffusion hardening performed according to step (a) or (b): (a) diffusion hardening to form a diffusion hardened metallic surface on one and only one of said first and second contacting surfaces; (b) diffusion hardening to form a diffusion hardened metallic surface on both of said first and second contacting surfaces wherein said first contacting surface is diffusion hardened with at least a first diffusion hardening species and said second contacting surface is diffusion hardened with at least a second diffusion hardening species and wherein said first diffusion hardening species is different from said second diffusion hardening species. In some embodiments, the step of forming a device comprises forming a medical implant. In some embodiments, the step of forming a device from a metal or metal alloy comprising a first portion and a second portion comprises forming said first portion and said second portion from different metal or metal alloys. In some embodiments, the metal or metal alloy is CoCr. In some embodiments, the said step of diffusion hardening comprises plasma hardening. In some embodiments wherein a medical implant is formed, said step of forming a medical implant comprises forming a hip implant. In some embodiments wherein a hip is formed, one of said first portion and said second portion is an acetabular component and the other of said first portion and said second portion is a femoral component. In some embodiments wherein a medical implant is formed, said step of forming comprises forming a knee implant. In some embodiments wherein a knee implant is formed, one of said first portion and said second portion is a tibial component and the other of said first portion and said second portion is a femoral component. In some embodiments wherein a medical implant is formed, said step of forming a medical implant comprises forming a medical implant selected from the group consisting of a shoulder implant, an elbow implant, a finger implant, a vertebral implant, and a tempro-mandibular implant. In some embodiments, the method further comprises the step of depositing a ceramic coating on one or both of said first and second contacting surfaces. In some embodiments, the method further comprises the step of depositing a diamond or diamond-like carbon coating on one or both of said first and second contacting surfaces. In some embodiments, the step of diffusion hardening to form a diffusion hardened metallic surface on both of said first and second contacting surfaces comprises forming a diffusion carburized and diffusion oxidized surface on said first contacting surface and forming a diffusion carburized surface on said second contacting surface. In some embodiments wherein step (b) applies, said step of diffusion hardening for said first contacting surface is performed with a diffusion hardening species selected from the group consisting of carbon, nitrogen, boron, and any combination thereof; and, said step of diffusion hardening for said second contacting surface is performed with a diffusion hardening species selected from the group consisting of carbon, nitrogen, oxygen, boron, and any combination thereof, subject to the condition that one of said contacting surfaces is diffusion hardened with a diffusion hardening species that is not present as a diffusion hardening species in the other contacting surface. In some embodiments, said step of diffusion hardening to form a diffusion hardened metallic surface is performed with a diffusion hardening species selected from the group consisting of carbon, nitrogen, oxygen, and any combination thereof.

In another embodiment, there is a medical implant comprising: a first portion, said first portion having a first contacting surface; a second portion, said second portion having a second contacting surface; wherein the first portion and the second portion are comprised of metal or metal alloy, and wherein the first and second contacting surfaces contact one another; and, wherein one of conditions (a) and (b) is met: (a) one of said first and second contacting surfaces comprises a diffusion hardened surface and the other of said first and second contacting surfaces' is not diffusion hardened; (b) both of said first and second contacting surfaces comprise a diffusion hardened surface wherein said first contacting surface is diffusion hardened with a first diffusion hardening species and said second contacting surface is diffusion hardened with a second diffusion hardening species and wherein said first diffusion hardening species is different from said second diffusion hardening species; wherein the diffusion hardened surfaces in (a) and (b) are selected from the group consisting of diffusion carburized surfaces and diffusion nitrided surfaces. In some embodiments, the metal or metal alloy comprising said first portion is different from said metal or metal alloy comprising said second portion. In particular embodiments, the metal or metal alloy is CoCr. In particular embodiments, the diffusion hardened surface is a plasma hardened surface. In some embodiments, the plasma hardened surface is selected from the group consisting of a plasma carburized surface, a plasma nitrided surface and a surface both plasma carburized and plasma nitrided. In some embodiments, the medical is a hip implant. In particular embodiments of a hip implant, the first portion is a femoral component comprising a stem and a femoral head and wherein said femoral head comprises said first contacting surface; wherein said second portion is an acetabular component, said acetabular component comprising a inner surface and wherein said inner surface comprises said second contacting surface. In particular embodiments of the hip implant, the diffusion hardened surface is a plasma hardened surface. In particular embodiments of the hip implant, the plasma hardened surface is selected from the group consisting of a plasma carburized surface, a plasma nitrided surface and a surface both plasma carburized and plasma nitrided. In some embodiments, the medical implant is a knee implant. In particular knee implant embodiments, the first portion is a femoral component comprising at least one condyle, said at least one condyle comprising said first contacting surface, and wherein said second portion is a tibial component, said tibial component comprising said second contacting surface. In particular embodiments of the knee implant, the diffusion hardened surface is a plasma hardened surface. In particular embodiments of the knee implant, the plasma hardened surface is selected from the group consisting of a plasma carburized surface, a plasma nitrided surface and a surface both plasma carburized and plasma nitrided. In other embodiments, the medical implant is selected from the group consisting of a shoulder implant, an elbow implant, a finger implant, a vertebral implant, and a tempro-mandibular implant. In particular embodiments, the first contacting surface and said second contacting surface articulate against one another. In some embodiments, the implant further comprises a ceramic coating on one or both of said first and second contacting surfaces. In some embodiments, the implant further comprises a diamond or diamond-like carbon coating on one or both of said first and second contacting surfaces.

In another embodiment of the present invention, there is a medical implant comprising: a first portion, said first portion having a first contacting surface; a second portion said second portion having a second contacting surface; wherein the first portion and the second portion are comprised of metal or metal alloy, and wherein the first and second contacting surfaces contact one another; and, wherein one of conditions (a) and (b) is met: (a) one of said first and second contacting surfaces comprises a diffusion oxidized surface and the other of said first and second contacting surfaces is not diffusion hardened; (b) one of said first and second contacting surfaces comprise a diffusion oxidized surface and the other of said first and second contacting surfaces is diffusion carburized, diffusion nitrided, or both diffusion carburized and diffusion nitrided. In some embodiments, the first contacting surface and said second contacting surface articulate against one another. In particular embodiments, the metal or metal alloy is CoCr. In some embodiments, the medical implant is a hip implant. In some embodiments, the medical implant is a knee implant. In particular embodiments, the implant further comprises a ceramic coating on one or both of said first and second contacting surfaces. In some embodiments the medical implant further comprises a diamond or diamond-like carbon coating on one or both of said first and second contacting surfaces.

In another embodiment of the present invention, there is a method of making a medical implant comprising the steps of: forming a medical implant from a metal or metal alloy, said medical implant comprising a first portion, said first portion having a first contacting surface, and a second portion, said second portion having a second contacting surface, wherein said first and second contacting surfaces contact one another; diffusion hardening said medical implant according to step (a) or (b): (a) diffusion hardening one and only one of said first and second contacting surfaces; (b) diffusion hardening both of said first and second contacting surfaces wherein said first contacting surface is diffusion hardened with a first diffusion hardening species and said second contacting surface is diffusion hardened with a second diffusion hardening species and wherein said first diffusion hardening species is different from said second diffusion hardening species; wherein the diffusion hardened surfaces in (a) and (b) are selected from the group consisting of diffusion carburized surfaces and diffusion nitrided surfaces. In some embodiments, the first portion comprises a different metal or metal alloy from said second portion. In particular embodiments, the metal or metal alloy is CoCr. In particular embodiments, the step of diffusion hardening comprises plasma hardening. In some embodiments, the step of forming a medical implant comprises forming a hip implant. In some embodiments, the step of forming comprises forming a knee implant. In some embodiments, the step of forming a medical implant comprises forming a medical implant selected from the group consisting of a shoulder implant, an elbow implant, a finger implant, a vertebral implant, and a tempro-mandibular implant. In some embodiments, the method further comprises the step of depositing a ceramic coating on one or both of said first and second contacting surfaces. In some embodiments, the method further comprises the step of depositing a diamond or diamond-like carbon coating on one or both of said first and second contacting surfaces.

In another embodiment of the present invention, there is a method of making a medical implant comprising the steps of: forming a medical implant from a metal or metal alloy, said medical implant comprising a first portion, said first portion having a first contacting surface, and a second portion, said second portion having a second contacting surface, wherein said first and second contacting surfaces contact one another, diffusion hardening said medical implant according to step (a) or (b): (a) diffusion oxidizing one and only one of said first and second contacting surfaces and not diffusion hardening the other of said first and second contacting surfaces; (b) diffusion oxidizing one of said first and second contacting surfaces and diffusion hardening the other of said first and second contacting surfaces; wherein the step of diffusion hardening in (b) is selected from the group consisting of diffusion carburized surfaces and diffusion nitrided surfaces. In some embodiments, the said first portion comprises a different metal or metal alloy from said second portion. In particular embodiments, the metal or metal alloy is CoCr. In some embodiments, the diffusion hardened surface is a plasma hardened surface, said diffusion oxidized surface is a plasma oxidized surface or said diffusion hardened surface is a plasma hardened surface and said diffusion oxidized surface is a plasma oxidized surface. In some embodiments, the step of forming a medical implant comprises forming a hip implant. In some embodiments, the step of forming comprises forming a knee implant. In some embodiments, the step of forming a medical implant comprises forming a medical implant selected from the group consisting of a shoulder implant, an elbow implant, a finger implant, a vertebral implant, and a tempro-mandibular implant. In some embodiments, the method further comprises the step of depositing a ceramic coating on one or both of said first and second contacting surfaces. In some embodiments, the method further comprises the step of depositing a diamond or diamond-like carbon coating on one or both of said first and second contacting surfaces.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
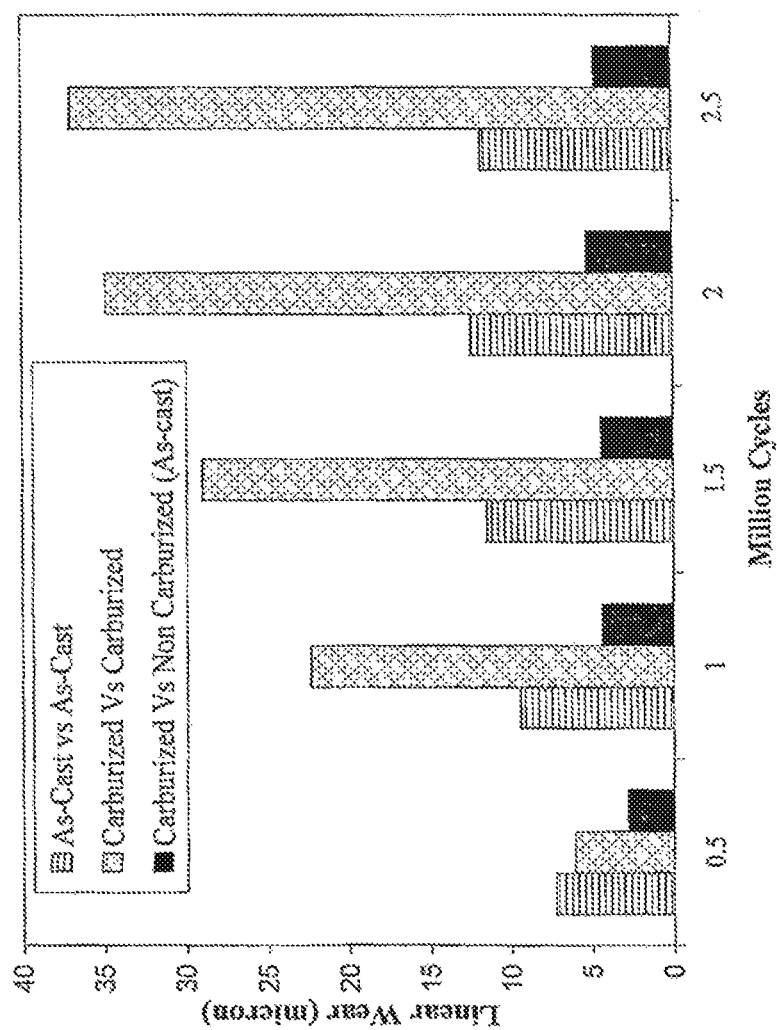
FIG. 1 shows linear wear of as-cast and plasma carburized metal-on-metal couples tested in a hip simulator.

As used herein, "a" or "an" means one or more. Unless otherwise indicated or is clear by the context, the singular contains the plural and the plural contains the singular.

As used herein, the term "articulating" as it refers to multiple medical implant surfaces means surfaces that contact each other in a primary load-bearing manner. The term "contacting" as used herein as it refers to multiple medical implant surfaces refers to any surface of the implant which contacts another surface of the implant, including both load-bearing contact (such are articulating surfaces) and non-load bearing contact. Thus, the term "contacting surface" is broader than, and encompasses the term "articulating surface." The term "contacting" refers to all forms of contact and also encompasses intermediate forms of contact such as contact in secondary load bearing manner. Such medical implant surfaces are said to be contacting surfaces. Where an implant surface is said to be used against another implant surface it should be understood to mean that the two surfaces are placed in a position such that they are contacting surfaces with respect to one another. Contacting surfaces in a medical implant are said to be "coupled to" one another.

As used herein, "implant portion" refers to any part of a medical implant. Implant portions of a medical implant may be separate (detached) portions or may be separate portions of a unitary implant.

As used herein, "diffusion hardening" means the general technique of hardening a metal or metal alloy by diffusing a hardening species into the surface of the metal or metal alloy and into or towards the bulk of the metal or metal alloy. Diffusion hardening encompasses "conventional diffusion hardening", whereby a diffusion hardening species in the gas, liquid or solid phase is brought into contact with a metal or metal alloy, usually at elevated temperatures, and "plasma hardening", whereby a diffusion hardening species in a plasma is brought into contact with a metal or metal alloy to effect diffusion of the species into the metal or metal alloy. The diffusion hardening species in the present invention are limited to carbon, nitrogen, boron, and oxygen. Thus, diffusion hardening herein results in a carburized surface, a nitrided surface, an oxidized surface, a borided surface, or any combination thereof. Herein, "plasma hardened" means plasma carburized, plasma nitrided, plasma borided, plasma oxidized or any combination thereof. A "plasma hardened surface" means a plasma carburized surface, a plasma nitrided surface, a plasma borided surface, a plasma oxidized surface, or any combination thereof.

As used herein, a "diffusion hardened metallic surface" is defined as metal or metal alloy surface has been diffusion hardened in such a way as to either avoid formation of a ceramic layer on the surface, or to remove any such layer formed during the diffusion hardening process. A "diffusion hardened ceramic surface" is one which results when a metal or metal alloy is subject to a diffusion hardening process that results the formation of a surface ceramic layer. In this way, a diffusion hardened surface differs from a diffusion hardened ceramic surface.

As used herein, CoCr alloy is defined broadly, and includes alloys having at least 20% (w/w) chromium and at least 50% cobalt. The balance elements can be molybdenum, tungsten, iron, nitrogen and carbon. The typical alloys of this composition are described in ASTM international standards F799, F1537, F75 and F90 (ISO 5832-4 to ISO 5832-8). Although most of the discussion focuses on CoCr alloys, it should be understood that the present invention is not so limited and is applicable to any metal or metal alloy and in the context of medical implants, it is preferable that the metal or metal alloy be a biocompatible metal or metal alloy such as those commonly used in orthopaedic applications.

As used herein, "carburized layer" is defined is a layer of a metal or metal alloy comprising a solid solution of the substrate metal or metal alloy and carbon. The substrate is diffused with carbon to form the solid solution. It should be noted that it is also within the scope of this invention to use a nitrided layer (diffused with nitrogen), an oxidized layer (diffused with oxygen), a borided layer (diffused with boron), and combination layers using any combination of carburization, nitridation, oxidation, and boridation. Although much of the discussion herein focuses on carburization, however, it should be understood that the present invention includes metallic hardening with any of, or any combination of, interstitial elements of carbon, nitrogen, oxygen, and boron. Thus, in addition to a carburized layer, one may also have an oxidized layer, a nitrided layer, a borided layer, and combinations thereof. Although carbon, nitrogen, oxygen and boron are all useful in, and encompassed by, the present invention, carbon is most preferred and boron is least preferred. In some embodiments of the invention, therefore, the use of boron to form a borided layer is eliminated.

There has been a growing need of implants with less wear for young and active patients. The conventional implants employ polyethylene and a metallic or ceramic counterface. Although wear of these implants is significantly low, they do have limitations. One of the limitations is size of the implant. In order to achieve stability and greater range of motion for young and active patients, there has been a trend for larger sized implants. This has led to emergence of metal-on-metal implants. The typical metal-on-metal implants are made of high carbon CoCr alloy. Although they offer significantly lower wear rates, the metal ion release from these implants and its effect on human physiology is still a concern. As mentioned previously, it has been object of several inventions to reduce this wear.

Conventional diffusion hardening of metals and metals alloys for orthopaedic applications is known in the art. The use of diffusion-hardened oxide surfaces such as oxidized zirconium in orthopedic applications was first demonstrated by Davidson in U.S. Pat. No. 5,037,438. The Davidson '438 patent discloses a method of producing zirconium alloy prostheses with an oxidized zirconium surface. U.S. Pat. No. 2,987,352 to Watson discloses a method of producing zirconium bearings with a oxidized zirconium surface. The oxide coating produced is not always uniform in thickness and the non-uniformity reduces the integrity of the bonding between the zirconium alloy and the oxide layer and the integrity of the bonding within the oxide layer. Davidson and Watson both teach diffusion hardening of zirconium alloys. In the general method, a zirconium alloy is heated in air at elevated temperature. Heating in air leads to diffusion of oxygen in the substrate and thus forms the ceramic oxide on the surface. In another approach Shetty et. al. (U.S. Pat. No. 5,308,412) teach nitrogen diffusion hardening of CoCr alloys. Shetty teach heating CoCr alloy in nitrogen enriched environment (ionic or molecular) for prolonged periods of time to diffusion harden the surface with nitrogen. U.S. Pat. No. 5,152,794 to Davidson extends the concept of conventional diffusion hardening to diffusion nitriding (using a nitrogen source for the nitridation). U.S. Pat. Nos. 2,987, 352; 5,037,438; 5,308,412; and 5,152,794 are incorporated by reference as though fully set forth herein.

In U.S. Pat. Nos. 6,447,550; 6,585,772 and pending U.S. application Ser. No. 10/942,464, Hunter, et al. describes methods for obtaining an oxidized zirconium coating of uniform thickness. Hunter teaches that such is obtained by applying pre-oxidation treatment techniques and by manipulation of substrate microstructure. The use of uniform thickness oxide layer results in increased resistance to corrosion by the action of the body fluids as well as other benefits and is biocompatible and stable over the lifetime of the recipient. U.S. Pat. Nos. 6,447,550; 6,585,772 and pending U.S. application Ser. No. 10/942,464 are incorporated by reference as though fully set forth herein. Hunter et. al. teach two approaches to obtain a uniform oxide. One approach is to achieve an adequate surface roughness as pre-oxidation step. This surface roughness allows diffusion of oxygen uniformly to create an adherent and uniform oxide on the surface. In another approach Hunter teach use of a refined fined grained microstructure. The purpose here is also to allow diffusion of oxygen uniformly in to the substrate and thus lead to uniform adherent oxide. However, it should be understood that the compositions of Davidson, Watson, and Hunter were diffusion hardened ceramic surfaces. The surfaces of the present differ in that they are diffusion hardened metallic surfaces which is explained below.

The conventional diffusion hardening processes of Davidson and Hunter allow interstitial elements (such as C, N, O, and/or B) to diffuse in to the metallic surface. As these elements diffuse in the surface it may saturate the metal surface and thus lead to hardening of the surface. If the diffusion is continued further beyond the solubility limit of the interstitial element in the substrate it can lead to formation of a ceramic surface or a compound formation along with a diffusion hardened zone. An example of which is Davidson and Hunter process that leads to formation of the oxide on Zr alloy surface. It is the object of this invention to only form diffusion hardened metallic surface and not form a ceramic layer or compound on the surface. If the ceramic layer or compound is formed during the conventional process, it can be removed by known techniques in the art. It is known to those skilled in the art that a diffusion process can be carried out by several means. The conventional diffusion hardening processes that are known in the art are pack carburizing or nitriding, salt bath carburizing or nitriding or using gaseous mixtures of diffusing species. For example, a device made from CoCr alloy is heated in presence of 100% nitrogen gas at temperature ranging from 250° C. to 1000° C. for extended periods of time. The longer diffusion times will create thicker diffusion hardening zone. The typical time of hardening can be 5 hours or more. The device can be placed in a natural convection oven or can alternatively be heated by resistive heating. After such prolonged treatment a diffusion hardened zone is formed along with a thin ceramic layer (chromium nitride) on the surface. This ceramic layer is now removed by polishing with grinding medium such as but not limited to silicon carbides or alumina or silica. It is the object of this invention to create a surface that is diffusion hardened and is metallic in nature Another processes in the art for diffusion hardening is plasma hardening. It should be understood by those skilled in the art that the objective is to have the presence of diffusion specie either in the solid or liquid or gaseous or plasma forms or combinations thereof. For example, nitrogen diffusion hardening of Ti alloys can be carried out in a nitrogen rich atmosphere or in nitrogen gas plasma. If nitrogen diffusion is carried out for long times of titanium nitrides on the surface. While conventional diffusion hardening sometimes results in a ceramic coating on the surface, it is the object of this invention to allow the saturation only to the extent that the ceramic layer is not formed or if it is formed it is removed by mechanically, or by heating the surface in the absence of a diffusion hardening species such that diffusion hardening species is driven deeper into the substrate, thereby consuming any ceramic layer which may have formed. The examples of mechanical removal of the ceramic layer include grinding with abrasive media such as silicon carbide, alumina or silica. Although most of the ceramic surfaces will be difficult to remove by acids or alkalies, chemical-mechanical polishing methods can be used. The chemical polishing methods employ abrasive media suspended in acidic or alkaline medium which will enhance removal rates of ceramic surface. Alternatively, formation of a ceramic layer in conventional diffusion hardening processes may be avoided by judicious control of the process variables (time, temperature, concentration of diffusion hardening species, etc.) avoid ceramic layer formation. It may be necessary to modify the variables of the conventional diffusion hardening process depending upon the nature of the metal or metal alloy substrate, the nature of the diffusion hardening species, and possibly other factors. In some cases, it may be necessary to run a sample under a set of conditions, then perform analytical tests on the sample to determine the presence of and the extent of ceramic layer formation. The presence of ceramic layer can be determined by conventional cross-sectional metallographic techniques. It can also be determined from the chemical composition of the surface and based on the solubility of diffusing specie in that alloy system. The solubility of the diffusing specie in-turn can be obtained from the phase diagrams. The presence of ceramic layer can also be determined using a capacitance-voltage measurement of the sample. Since a ceramic layer is typically a insulator a ceramic layer on the surface of a metal creates a capacitor. Alternatively ceramic layer or its thickness can be measured using depth profiling and x-ray photoelectron spectroscopy (XPS). In XPS, the valence state of the diffusing specie can be determined which in turn can help in estimating the depth of the ceramic layer. Other analytical techniques, particularly surface analysis techniques, known to those of ordinary skill in the art are applicable. Process variables can then be modified to preclude formation of the ceramic. Similarly, when removing a ceramic by mechanical, chemical, or heat treatment, one may perform analytical tests on the sample to determine the extent of ceramic layer removal. In the present invention, wherein a diffusion hardened surface is formed using that conventional diffusion hardening processes of Davidson, Watson, and Hunter, it is required that the final product is a diffusion hardened metallic surface and not a diffusion hardened ceramic surface.

As discussed, another mechanism for diffusion hardening of metals and metal alloys to produce a diffusion hardened metallic surface comprises the surface modification of these materials by the incorporation of non-metallic species by treatment of the metal or metal alloy with such species in a plasma. A plasma is typically an ionized gas (atoms or molecules), and is usually considered to be a distinct phase of matter in contrast to solids, liquids, and gases because of its unique properties. The ionization of the gaseous atoms or molecules results in at least one electron being dissociated from a proportion of the atoms or molecules. The resulting free electric charges make the plasma electrically conductive so that it responds strongly to electromagnetic fields. Plasmas may be created by electromagnetic fields (e.g., RF or microwave plasmas) or by voltage discharges (e.g., glow discharge). In some cases, like that discussed for conventional diffusion hardening, it may be necessary to either avoid ceramic layer formation or remove any such layer. This is analogous to the situation discussed for conventional diffusion hardening. Removal techniques are the same as those for samples which are diffusion hardened conventionally. Also similar to conventional diffusion hardening, it may be necessary to modify the variables of the plasma hardening process depending upon the nature of the metal or metal alloy substrate, the nature of the diffusion hardening species, and possibly other factors. In some cases, it may be necessary to run a sample under a set of conditions, then perform analytical tests on the sample to determine the presence of and the extent of ceramic layer formation.

Plasma hardening of CoCr alloy using carbon has been described previously by Bell et. al (U.S. Patent Application No. 2005/0241736 A1). Diffusion hardening using nitrogen has been taught by Shetty et. al. (U.S. Pat. No. 5,308,412). The '736 patent application describes the carburization process. It further states that such processed implants can be used in knee or hip joints. The '412 patent describes the nitridation process. It should be noted that both these inventions do not anticipate the coupling of such a hardened implant to a non-hardened implant. U.S. Patent Application No. 2005/0241736 A1 and U.S. Pat. No. 5,308,412 are incorporated by reference as though fully set forth herein.

However, surface hardening by carburization and/or nitridation and/or oxidation and/or boridation can be performed by any and all methods known in the art. The preferred embodiments use the conventional diffusion hardening or plasma hardening techniques discussed above. The present invention includes carburization, nitridation, boridation, oxidation, and combinations thereof, of surfaces of metallic devices generally, and of medical implants specifically, particularly, those surfaces of medical implants and metallic devices subject to wear such as articulating surfaces.

Generally, plasma treatment in the context of the present invention means exposing a metal or metal alloy to a plasma in the presence of a carbon source, an oxygen source, a nitrogen source, a boron source, or any combination thereof. Examples of a carbon source include methane; examples of a nitrogen source includes nitrogen gas; examples of an oxygen source include oxygen gas and air. The examples of boron source include but not limited to amorphous boron, boric acid ($B_2O_3$), and boron trichloride ($BCl_3$). These are merely illustrative examples of sources of diffusion species, others known to those of skill in the art are also applicable. The same sources are useful in conventional diffusion hardening techniques.

One exemplary, non-limiting procedure is provided for the plasma carburization of a medical implant. An implant is placed on a surface inside a vessel, the surface being connected as a cathode to a power supply and control unit, and the wall of the vessel is connected to the direct current source as the anode. The temperature of the implant was measured by the thermocouple inserted into a hole of 3 mm diameter drilled in an implant portion or a dummy sample. After the sealable vessel is tightly closed, a rotary pump is used to remove the residual air (oxygen) and thus reduce the pressure in the vessel. When the reduction in pressure reaches 10 Pa (0.1 mbar) or less, a glow discharge was introduced between the implant and the vessel wall (anode) by applying a voltage of about 400 volts to about 900 volts between these two electrodes. A heating gas of hydrogen was at the same time introduced into the vessel. The pressure of the hydrogen gas in the vessel is increased gradually as the temperature of the implant increases. No external or auxiliary heating is employed, and the implant is heated by the glow discharge plasma only. Alternatively, an external heat source may be used.

In other embodiments, an external heater attached to the vessel may be employed, or a combination of external heating and electrical glow discharge heating may be employed. Direct current (dc) discharge, pulsed dc discharge or alternating current (ac) discharge may be used.

After the implant is heated to the prescribed temperature, a gas mixture of hydrogen (98.5%) and methane (1.5%) is introduced into the vessel and the plasma treatment started. Treatment temperatures from about 400° C. to about 600° C. are employed for a treatment time of 10 hours. The working pressure in the treatment step is 500 Pa (5.0 mbar).

During the plasma heat treatment, the methane is ionized, activated and dissociated to produce carbon ions and activated carbon atoms and neutral molecules, which then diffuse into the surface of the disc forming a carbon diffusion layer. When the plasma treatment is carried out at a relatively low temperature ranging from 300 to 550° C., the carbon atoms mainly reside in the cobalt lattices, forming a supersaturated solid solution with a possible nanocrystalline structure due to the relatively low temperatures employed in the treatment. The resultant layer has a high hardness, good fatigue strength and excellent wear and corrosion resistance (see below). When the plasma treatment is carried out at a relatively high temperature ranging from 600 to 700° C., the carbon atoms partially reside in the cobalt lattices forming a supersaturated solid solution and partially combined with carbon forming chromium carbides. The resultant layer has a high hardness, fatigue strength and excellent wear resistance.

After the completion of the plasma treatment, the glow discharge plasma is turned off and the implant is allowed to cool in the vessel in the treatment atmosphere down to room temperature before they were removed from the vessel. Treatment times and temperatures may be varied to achieve the desired level of nitridation. For nitridation of the implant, the same procedure can be used with a gas mixture of hydrogen and nitrogen, or nitrogen alone. Again, treatment times and temperatures may be varied to achieve the desired level of nitridation. Finally, it is possible to use both the nitrogen and carbon source (for example a mixture of methane, hydrogen and nitrogen, etc.) for both carburize and nitride. Alternatively, separate carburization and nitridation steps may be performed sequentially on the same implant portion.

It should be understood that the example provided above is merely illustrative and not exhaustive; any known or yet to be developed plasma nitridation and/or carburization procedures may be used. All that is required is that a sufficient degree of carburization and/or nitridation of a metal or metal alloy (preferably CoCr) surface is applicable in the present invention. In some embodiments of the invention, it is preferential to form carburized or nitrided layer at least 1 micron thick.

The inventors have unexpectedly found that the wear performance of first and second contacting metallic surfaces of medical implants, (particularly where the contacting surfaces are articulating surfaces) is significantly lower, when the first contacting surface is a diffusion hardened metallic surface and the second contacting surface is either 1) not diffusion hardened or 2) diffusion hardened using a hardening species different from that used in the first contacting surface. In the present invention, where a surface is diffusion hardened, it is diffusion hardened to form a diffusion hardened metallic surface. The reason for the lower wear is not completely clear. Although not wishing to be bound by theory, it is possible that the differential hardness of the contacting surfaces (owing to the differing treatment of the surfaces) and/or the different compositions of the first and second contacting surfaces may play a role in the beneficial effect seen. It has been observed that a plasma carburized CoCr surface contacting a non-carburized CoCr surface in a load bearing manner exhibits superior wear characteristics when compared to a non-plasma carburized CoCr surface against another non-plasma carburized CoCr surface, and also as compared to a plasma carburized CoCr surface against another plasma carburized CoCr surface.

Figure 2:
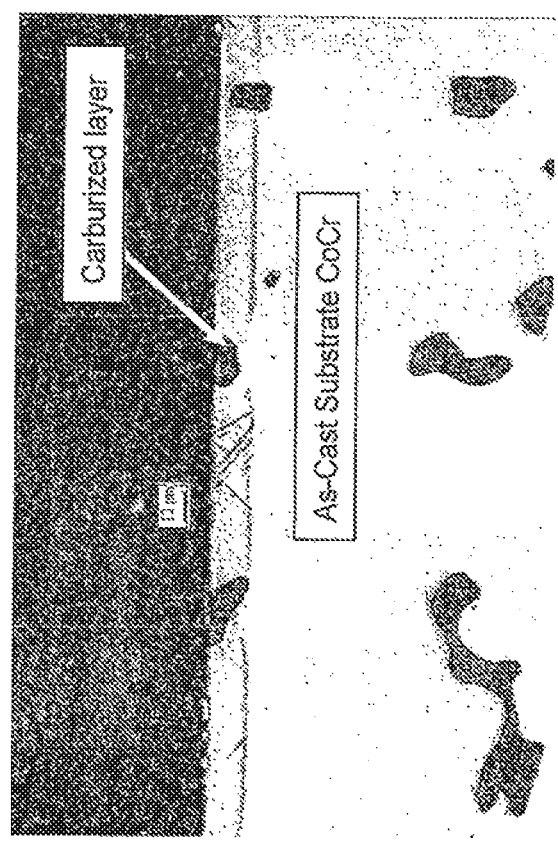
FIG. 2 shows a metallographic image of carburized layer on as-cast CoCr alloy sample.

FIG. 1 shows linear wear of as-cast and plasma carburized CoCr metal-on-metal couples tested in a hip simulator. The linear wear of as-cast articulating against as-cast metal-on-metal couple is 7 micron at the end of 0.5 Mcycles. It increases to 10 microns at the end of 1 Mcycle. It then reaches a steady state and stabilizes at 10 microns. The inventors have found that this wear rate can be significantly reduced if only one of the mating couple is selectively hardened for example, using carburization process. As shown in FIG. 2, the linear wear when the femoral head is carburized and acetabular shell is not carburized is approximately 3 microns and stabilizes at 5 microns up to 2.5 Mcycle. Thus leads to approximately 50% reduction in linear wear. As shown in FIG. 1, the inventors have found that when both couples are selectively hardened, the wear is actually more than when they are not hardened. The linear wear of both components that are carburized is approximately 6 microns at 0.5 Mcycle. It increases to 23 microns at the end of 1 Mcycle and reaches approximately 35 microns at the end of 2.5 Mcycles. The reduction in wear of the mating couple by selectively hardening one component of the couple is a particular embodiment of this invention. It will be understood by those skilled in the art that similar results can be obtained if one of the couple had been nitrided.

In an embodiment of the invention, the substrate alloy that is being carburized can be as-cast, FIG. 2 shows a metallographic image of the carburized layer of as-cast component. The carburized layer is approximately 8 micron thick. As a preferred embodiment of this invention, the carburized component is coupled with non-carburized component. The non-carburized component can be as-cast or is machined from a wrought bar stock. Alternatively, it can be made from a forged component. It should be noted that a particular embodiment of this invention is to take advantage of the differences in the surface hardness/compositional characteristics of the mating components.

Alternatively, the substrate alloy that is being carburized is machined from wrought bar stock or is forged. This carburized component is then coupled with non-carburized component. The non-carburized component can be as-cast or is machined from a wrought bar stock. Alternatively, it can be made from a forged component.

In an embodiment of invention, the carburized layer thickness is from 1 to 25 microns. In as-cast components, the carburized layer may encompass the substrate carbides as shown in FIG. 2. In wrought components, the carburized layer may or may not encompass fine carbides based on the pre-carburization heat treatment of the substrate alloy. In one aspect of invention the carburized layer is approximately 1.2 times harder than the substrate alloy.

Although the example of FIG. 1 showed the unexpected improvement in wear performance that is realized in using plasma carburized CoCr surface against an untreated (as cast) CoCr surface, the present invention is not so limited. Although not wishing to be bound by theory, it is suspected that the improvement is based upon the differential hardness between the plasma carburized CoCr surface and the untreated (as cast) CoCr surface. Accordingly, it is suspected that the use of differential treatment of cooperating surfaces will result in wear performance improvement in any hard-on-hard couple. For example, it is also within the scope of the present invention to have a medical implant having plasma carburized CoCr surface cooperating against a plasma nitrided CoCr surface. Because two different diffusion species are used, a differential hardness in the cooperating surfaces will result. Other combinations of plasma hardened against another plasma hardened surface (hardened with a different species) are also within the scope of the present invention. For example, one may use a plasma oxidized CoCr against a plasma nitrided CoCr, etc. For plasma hardening, any of plasma carburization, plasma nitridation, and plasma oxidation are useful. Each can be used against a plasma hardened surface (hardened with one of the other diffusion hardening species) or alternatively, they can be used against an untreated CoCr surface. Finally, any one of a plasma carburized surface, a plasma nitrided surface, or a plasma oxidized surface may be used against a surface hardened with a conventional diffusion hardening technique. One example of this would be any of a plasma carburized surface, a plasma nitrided surface, or a plasma oxidized surface used against a Davidson-type diffusion hardened surface.

In some embodiments of the invention the diffusion hardened layer is used as a pre-treatment surface for deposition of ceramic coatings. It is important to draw a distinction between these embodiments (deposited ceramic coatings) and the in-situ ceramic coatings that can form during any diffusion hardening processes (both conventional diffusion hardening process and plasma hardening). The ceramic coatings can be oxides, nitrides, carbides, or borides. Examples of such coating include aluminum oxide, aluminum nitride, chromium carbide, chromium nitride, titanium carbide, titanium nitride and titanium carbonitride. Such coatings can be deposited by methods known in the art, such as, but not limited to physical vapor deposition (PVD) or chemical vapor deposition (CVD). The ceramic coated component is then coupled with a diffusion hardened or a non-diffusion hardened component in a medical implant. Alternatively, the hard ceramic coating is performed on a non-diffusion hardened component which is coupled with a diffusion hardened component.

In other embodiments of the invention, the diffusion hardened component is used as a surface for diamond or diamond like carbon coatings (e.g., nanocrystalline diamond) which is coupled with non-diffusion hardened component. Alternatively, the diffusion hardened component is coated with diamond or diamond like carbon coating which is coupled with a diffusion hardened component. Again the coatings of these embodiments, unlike ceramic coatings which may form in either a conventional diffusion hardening process or in a plasma hardening process, are not formed in-situ, but are rather deposited or otherwise placed on the previously formed diffusion hardened metallic surface.

In an embodiment of the invention, antimicrobial surface is created on the carburized surface. This is accomplished by impregnating carburized layer with silver ions. The silver ions can be impregnated with ion implantation or using diffusion processes. The silver impregnated carburized component is then coupled with non-carburized or ceramic coated carburized component.

The present invention also provides a low friction, wear resistant surface on the articulating surfaces of CoCr prosthetic devices. Illustrative examples of such articulating surfaces are shown in the schematic diagrams of FIGS. 3-6 which illustrate hip and knee prosthetic devices. It should be understood that FIGS. 3-6 merely represent illustrative examples and that the present invention is applicable to a wide variety of prosthetic implants. Other examples include shoulder implants, elbow implants, finger implants, vertebral implants, and a tempro-mandibular implants.

Figure 3:
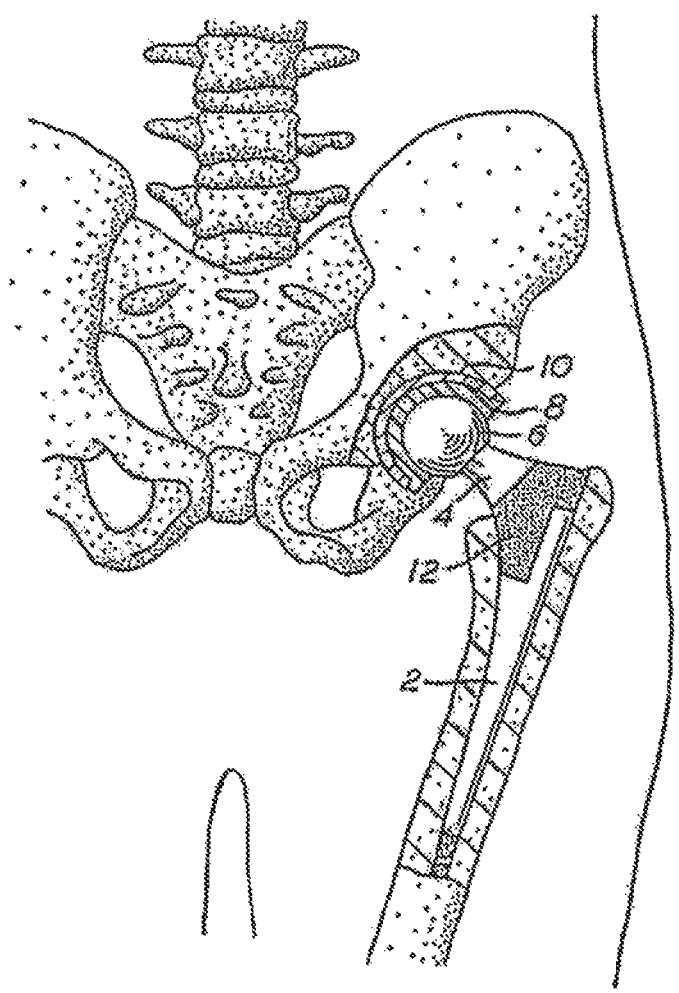
FIG. 3 is a schematic diagram depicting a hip joint prosthesis in situ.
Figure 4:
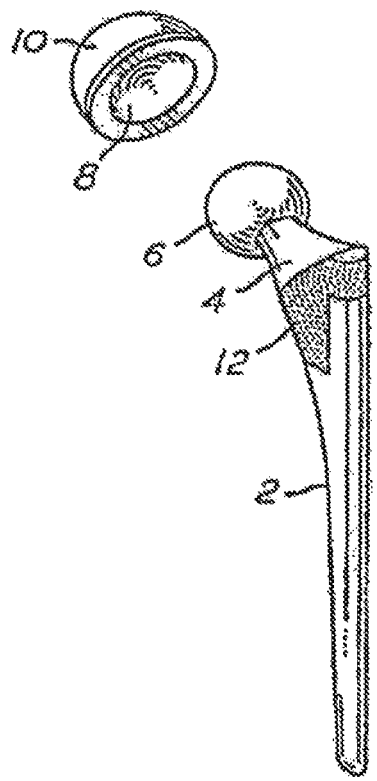
FIG. 4 is a schematic diagram showing a typical hip joint prosthesis ex situ.

A typical hip joint assembly is shown in situ in FIG. 3 and ex-situ in FIG. 4. The hip joint stem 2 fits into the femur while the femoral head 6 of the prosthesis fits into and articulates against the inner surface 8 of an acetabular cup 10 which in turn is affixed to the pelvis as shown in FIGS. 3 and 4. A porous metal bead or wire mesh coating 12 may be incorporated to allow stabilization of the implant by ingrowth of surrounding tissue into the porous coating. The femoral head 6 may be an integral part of the hip joint stem 2 or may be a separate component mounted upon a conical taper at the end of the neck 4 of the hip joint prosthesis. In this embodiment of a hip implant, the femoral head articulates against the inner surface of the acetabular cup thereby causing wear and, in the long term, this may necessitate prosthesis replacement. The inner surface can be in the form of a liner that fits in acetabular cup or can be an integral part of the acetabular component. In a preferred embodiment of the present invention, both the femoral head 6 and the acetabular cup 10 are made of CoCr alloy, whereas the surfaces of one and only one of either the femoral head 6 or the inner surface 8 of the acetabular cup 10 is diffusion hardened. This articulating couple exhibits unexpectedly low wear rates as compared to a CoCr surface (non-diffusion hardened) articulating against another CoCr surface (non-diffusion hardened) or a diffusion hardened CoCr surface articulating against another diffusion hardened CoCr surface. In other embodiments, both articulating surfaces are diffusion hardened, with the provision that one of the surfaces is diffusion hardened with a diffusion species which is not common to the other surface. For example, there may be a carbonitrided surface articulating against a carburized surface. In preferred embodiments, the diffusion hardening is accomplished through plasma hardening, preferably plasma carburization, although convention diffusion hardening and combinations of plasma hardening and diffusion hardening are applicable. Other diffusion hardening techniques known in the art are also applicable, both alone or in combination with plasma hardening and diffusion hardening. The embodiment of FIGS. 3 and 4 illustrate total hip arthroplasty. However, it should be understood that the present invention is applicable not only to total hip arthroplasty but also to resurfacing hip arthroplasty, such as but not limited to what is commercially known as Birmingham Hip Resurfacing. Resurfacing hip arthroplasty conserves bone by eliminating the large femoral stem of the total hip implant.

Figure 5:
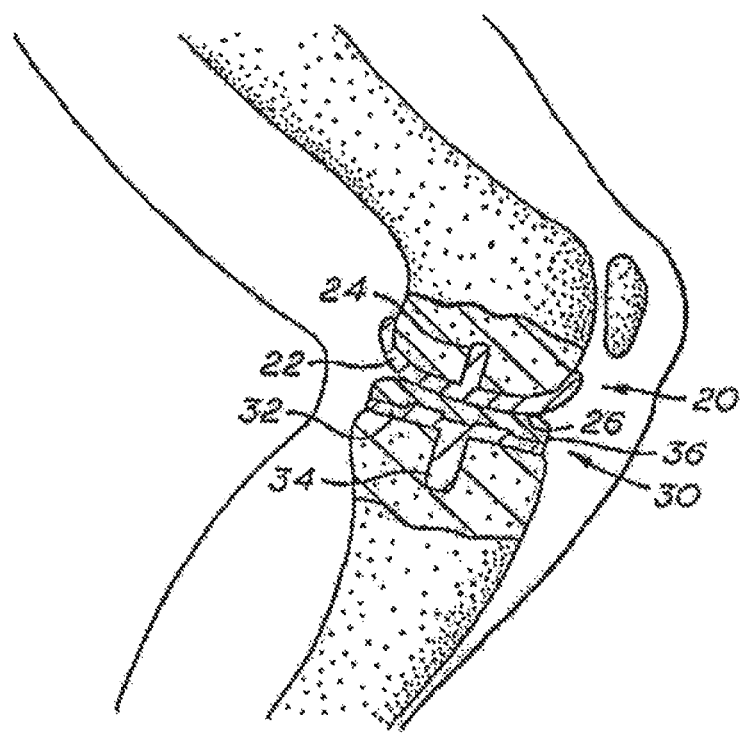
FIG. 5 is a schematic diagram of a typical knee joint prosthesis in situ.
Figure 6:
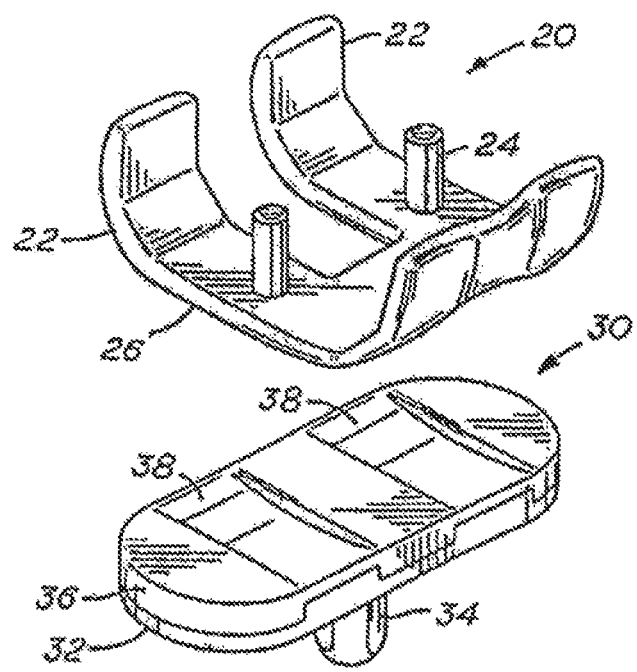
FIG. 6 is a schematic diagram showing a typical knee joint prosthesis ex situ.

A typical knee joint prosthesis is shown in situ in FIG. 5 and ex-situ in FIG. 6. The knee joint includes a femoral component 20 and a tibial component 30. The femoral component includes condyles 22 which provide the articulating surface of the femoral component and pegs 24 for affixing the femoral component to the femur. The tibial component 30 includes a tibial base 32 with a peg 34 for mounting the tibial base onto the tibia. A tibial platform 36 is mounted atop the tibial base 32 and is supplied with grooves 38 similar to the shape of the condyles 22. The bottom surfaces of the condyles 26 contact the tibial platform's grooves 38 so that the condyles articulate within these grooves against the tibial platform. As in the case of the hip joint, porous bead or wire mesh coatings can also be applied to either the tibial or femoral components of the knee or both. In a preferred embodiment of the present invention, both the femoral component 20 and the tibial component 30 are made of CoCr alloy, whereas one and only one of either the femoral component 20 and the tibial component 30 is diffusion hardened. Again, this articulating couple will exhibit unexpectedly low wear rates as compared to a CoCr surface (non-diffusion hardened) articulating against another CoCr surface (non-diffusion hardened) or a diffusion hardened CoCr surface articulating against another diffusion hardened CoCr surface. In other embodiments, both articulating surfaces are diffusion hardened, with the provision that one of the surfaces is diffusion hardened with a diffusion species which is not common to the other surface. For example, there may be a carbonitrided surface articulating against a carburized surface. In preferred embodiments, the diffusion hardening is accomplished through plasma hardening, preferably plasma carburization, although convention diffusion hardening and combinations of plasma hardening and diffusion hardening are applicable. Other diffusion hardening techniques known in the art are also applicable, both alone or in combination with plasma hardening and diffusion hardening.

It should be understood that although the preferred substrate in the implants and methods of the present invention is CoCr, the use of any metal or metal alloy substrate is within the scope of the present invention. For medical implant applications, such metals or metal alloys are preferably bio-compatible. Broadly, the scope extends to an implant having contacting surfaces of a metal or metal alloy, wherein one of the surfaces is diffusion hardened and the other contacting surface is either not diffusion hardened or is diffusion hardened with a diffusion hardened species not used in the opposing contacting surface.

Because of the superior wear characteristics of the metallic couple of the present invention, it has application is areas outside of medical implants. For example, the present invention is applicable in any applications wherein metallic components bear against one another. Non-limiting examples include parts and components (and devices in general) in the automotive and aerospace industries. Other commercial and industrial components are also applicable to the present invention and are encompassed by it. Other bearing applications would also benefit from an improved couple. It should be clear to one of ordinary skill in the art that other applications are encompassed herein, so long as there is involved a metallic-based couple that is subject to wear.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, and composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A device, comprising:
   a first portion, said first portion having a first contacting surface;
   a second portion, said second portion having a second contacting surface;
   wherein the first portion and the second portion are comprised of metal or metal alloy, and a deposited ceramic coating on one or both of said first and second contacting surfaces, wherein the first and second contacting surfaces contact one another; and
   wherein one of conditions (a) and (b) is met:
   (a) one of said first and second contacting surfaces comprises a diffusion hardened metallic surface which is diffusion hardened with a diffusion hardening species and the other of said first and second contacting surfaces is a metallic surface that is not diffusion hardened;
   (b) both of said first and second contacting surfaces comprise a diffusion hardened metallic surface wherein said first contacting surface is diffusion hardened with at least a first diffusion hardening species and said second contacting surface is diffusion hardened with at least a second diffusion hardening species and wherein said first diffusion hardening species is different from said second diffusion hardening species;
   wherein said diffusion hardening species is selected from the group consisting of carbon, nitrogen, oxygen, boron, and any combination thereof.

2. The device of claim 1, wherein said metal or metal alloy comprising said first portion is different from said metal or metal alloy comprising said second portion.

3. The device of claim 1, wherein one or both of said contacting surfaces comprises a plasma hardened surface.

4. The device of claim 1, wherein said device is a hip implant, one of said first portion and second portion is a femoral component comprising a femoral head and wherein said femoral head comprises a contacting surface; and
   wherein the other of said first portion and second portion is an acetabular component, said acetabular component comprising an inner surface wherein said inner surface comprises a contacting surface.

5. The device of claim 1, wherein said device is a knee implant, one of said first portion and second portion is a femoral component comprising at least one condyle, said at least one condyle comprising a contacting surface, and wherein the other of said first portion and second portion is a tibial component, said tibial component comprising a contacting surface.

6. The device of claim 1, wherein said first contacting surface and said second contacting surface articulate against one another.

7. The device of claim 1, wherein said deposited ceramic coating is selected from the group consisting of ceramic oxides, ceramic nitrides, ceramic carbides, ceramic borides, and any combination thereof.

8. The device of claim 1, wherein both of said first and second contacting surfaces comprise a diffusion hardened metallic surface and wherein said first contacting surface is diffusion carburized and diffusion oxidized, and said second contacting surface is diffusion carburized.

9. The device of claim 1, wherein condition (b) applies, and
   wherein said diffusion hardening species for said first contacting surface is selected from the group consisting of carbon, nitrogen, boron, and any combination thereof; and
   wherein said diffusion hardening species for said second contacting surface is selected from the group consisting of carbon, nitrogen, oxygen, boron, and any combination thereof; and
   subject to the condition that one of said contacting surfaces is diffusion hardened with a diffusion hardening species that is not present as a diffusion hardening species in the other contacting surface.

10. A device, comprising:
    a first portion, said first portion having a first contacting surface;
    a second portion, said second portion having a second contacting surface;
    wherein the first portion and the second portion are comprised of metal or metal alloy, and wherein the first and second contacting surfaces articulate against one another; and
    wherein one of conditions (a) and (b) is met:
    (a) one of said first and second contacting surfaces comprises a diffusion hardened metallic surface which is diffusion hardened with a diffusion hardening species and the other of said first and second contacting surfaces is a metallic surface that is not diffusion hardened;
    (b) both of said first and second contacting surfaces comprise a diffusion hardened metallic surface wherein said first contacting surface is diffusion hardened with at least a first diffusion hardening species and said second contacting surface is diffusion hardened with at least a second diffusion hardening species and wherein said first diffusion hardening species is different from said second diffusion hardening species;
    wherein said diffusion hardening species is selected from the group consisting of carbon, nitrogen, oxygen, boron, and any combination thereof; and
    wherein said first portion and said second portion are formed of different materials.

11. The device of claim 10, wherein one or both of said contacting surfaces comprises a plasma hardened surface.

12. The device of claim 10, wherein the device is a hip implant, one of said first portion and second portion is a femoral component comprising a femoral head and wherein said femoral head comprises a contacting surface; and
    wherein the other of said first portion and second portion is an acetabular component, said acetabular component comprising an inner surface wherein said inner surface comprises a contacting surface.

13. The device of claim 10, wherein said device is a knee implant, one of said first portion and second portion is a femoral component comprising at least one condyle, said at least one condyle comprising a contacting surface, and wherein the other of said first portion and second portion is a tibial component, said tibial component comprising a contacting surface.

14. The device of claim 10, wherein both of said first and second contacting surfaces comprise a diffusion hardened metallic surface and wherein said first contacting surface is diffusion carburized and diffusion oxidized, and said second contacting surface is diffusion carburized.

15. The device of claim 10, wherein condition (b) applies, and wherein said diffusion hardening species for said first contacting surface is selected from the group consisting of carbon, nitrogen, boron, and any combination thereof; and wherein said diffusion hardening species for said second contacting surface is selected from the group consisting of carbon, nitrogen, oxygen, boron, and any combination thereof; and subject to the condition that one of said contacting surfaces is diffusion hardened with a diffusion hardening species that is not present as a diffusion hardening species in the other contacting surface.

16. A device, comprising:

a first portion, said first portion having a first contacting surface;

a second portion, said second portion having a second contacting surface;

wherein one of said first and second portions comprises an acetabular cup, and wherein the other of said first and second portions comprises a femoral component;

wherein the first portion and the second portion are comprised of metal or metal alloy, and wherein the first and second contacting surfaces contact one another; and wherein one of conditions (a) and (b) is met:

(a) one of said first and second contacting surfaces comprises a diffusion hardened metallic surface which is diffusion hardened with a diffusion hardening species and the other of said first and second contacting surfaces is a metallic surface that is not diffusion hardened;

(b) both of said first and second contacting surfaces comprise a diffusion hardened metallic surface wherein said first contacting surface is diffusion hardened with at least a first diffusion hardening species and said second contacting surface is diffusion hardened with at least a second diffusion hardening species and wherein said first diffusion hardening species is different from said second diffusion hardening species; and wherein said diffusion hardening species is selected from the group consisting of carbon, nitrogen, oxygen, boron, and any combination thereof.

17. The device of claim 16, wherein said metal or metal alloy comprising said first portion is different from said metal or metal alloy comprising said second portion.

18. The device of claim 16, wherein one or both of said contacting surfaces comprises a plasma hardened surface.

19. The device of claim 16, wherein said first contacting surface and said second contacting surface articulate against one another.

20. The device of claim 16, wherein both of said first and second contacting surfaces comprise a diffusion hardened metallic surface and wherein said first contacting surface is diffusion carburized and diffusion oxidized, and said second contacting surface is diffusion carburized.

21. The device of claim 16, wherein condition (b) applies, and wherein said diffusion hardening species for said first contacting surface is selected from the group consisting of carbon, nitrogen, boron, and any combination thereof; and wherein said diffusion hardening species for said second contacting surface is selected from the group consisting of carbon, nitrogen, oxygen, boron, and any combination thereof; and subject to the condition that one of said contacting surfaces is diffusion hardened with a diffusion hardening species that is not present as a diffusion hardening species in the other contacting surface.

* * * * *